US012690918B2

(12) United States Patent
Baker et al.

(10) Patent No.: US 12,690,918 B2
(45) Date of Patent: Jul. 28, 2026

(54) SPECTRAL DETECTION OF OPTICAL FIBER FLASHING EVENT

(71) Applicant: GYRUS ACMI, INC., Westborough, MA (US)

(72) Inventors: Charles A. Baker, Rogers, MN (US); Sergey A. Bukesov, Acton, MA (US); Kurt G. Shelton, Bedford, MA (US); Kester Julian Batchelor, Mound, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 437 days.

(21) Appl. No.: 18/464,609

(22) Filed: Sep. 11, 2023

(65) Prior Publication Data

US 2024/0108410 A1     Apr. 4, 2024

Related U.S. Application Data

(60) Provisional application No. 63/377,646, filed on Sep. 29, 2022.

(51) Int. Cl.
| | |
|---|---|
| *A61B 18/22* | (2006.01) |
| *A61B 90/00* | (2016.01) |

(Continued)

(52) U.S. Cl.
CPC .............. *A61B 18/22* (2013.01); *A61B 90/37* (2016.02); *G01N 21/25* (2013.01);
(Continued)

(58) Field of Classification Search
CPC . A61B 18/22; A61B 2018/2255; A61B 90/37; A61B 2090/309; A61B 90/30;
(Continued)

(56) References Cited

U.S. PATENT DOCUMENTS

| | | |
|---|---|---|
| 4,785,806 A | 11/1988 | Deckelbaum |
| 5,199,431 A | 4/1993 | Kittrell et al. |

(Continued)

FOREIGN PATENT DOCUMENTS

| | | |
|---|---|---|
| CN | 111542893 A | 8/2020 |
| CN | 117770948 | 3/2024 |

(Continued)

OTHER PUBLICATIONS

"Japanese Application Serial No. 2023-170174, Response filed Feb. 7, 2025 to Notification of Reasons for Refusal mailed Sep. 9, 2024", w english claims, 14 pgs.

(Continued)

*Primary Examiner* — Aaron F Roane
(74) *Attorney, Agent, or Firm* — Schwegman Lundberg & Woessner, P.A.

(57)     ABSTRACT

A laser tissue ablation system can include an optical fiber, with a distal end being extendible from an endoscope body of an endoscope. The optical fiber can deliver therapeutic laser light from the distal end of the optical fiber toward a target site, and receive return light into the distal end of the optical fiber. The laser tissue ablation system can include a sensor that can spectrally measure the return light. The laser tissue ablation system can include processor circuitry that can form a first determination, from the spectral measurement of the return light, whether flashing event light is present in the return light. The flashing event light can be generated when a flashing event occurs at the distal end of the optical fiber. The processor circuitry can generate, in response to the first determination, a flashing event data signal that indicates whether the flashing event has occurred.

18 Claims, 4 Drawing Sheets

(51) Int. Cl.

| | | |
|---|---|---|
| *G01N 21/25* | (2006.01) | |
| *A61B 18/00* | (2006.01) | |
| *A61B 18/20* | (2006.01) | |
| *A61B 90/30* | (2016.01) | |

(52) U.S. Cl.
CPC ............... *A61B 2018/00577* (2013.01); *A61B 2018/00642* (2013.01); *A61B 2018/00696* (2013.01); *A61B 2018/00773* (2013.01); *A61B 2018/00898* (2013.01); *A61B 2018/2015* (2013.01); *A61B 2018/2205* (2013.01); *A61B 2090/309* (2016.02); *A61B 2217/007* (2013.01)

(58) Field of Classification Search
CPC ........... A61B 2018/00577; A61B 2018/00642; A61B 2018/00666; A61B 2018/00696; A61B 2018/00702; A61B 2018/00773; A61B 2018/00898; A61B 2018/2015; A61B 2018/2205; A61B 2217/007; G01N 21/25
USPC ........................................................ 606/15
See application file for complete search history.

(56) References Cited

U.S. PATENT DOCUMENTS

| | | | |
|---|---|---|---|
| 5,318,024 | A | 6/1994 | Kittrell et al. |
| 5,860,972 | A | 1/1999 | Hoang |
| 2021/0044079 | A1 | 2/2021 | Bukesov et al. |
| 2023/0033644 | A1 | 2/2023 | Bukesov et al. |
| 2024/0016543 | A1* | 1/2024 | Altshuler ............... A61B 18/22 |

FOREIGN PATENT DOCUMENTS

| | | |
|---|---|---|
| DE | 102023126616 | 4/2024 |
| WO | 2021026167 | 2/2021 |

OTHER PUBLICATIONS

"Japanese Application Serial No. 2023-170174, Final Notification of Reasons for Refusal mailed Mar. 4, 2025", 7 pgs.

"Japanese Application Serial No. 2023-170174, Notification of Reasons for Refusal mailed Sep. 9, 2024", w English Translation, 9 pgs.

"Japanese Application Serial No. 2023-170174, Response filed Jun. 3, 2025 to Final Notification of Reasons for Refusal mailed Mar. 4, 2025", w claims, 12 pgs.

"Indian Application Serial No. 202344065303, First Examination Report mailed Jan. 27, 2026", 12 pgs.

* cited by examiner

300

302 — ILLUMINATE

304 — CAPTURE VIDEO IMAGE

306 — DELIVER THERAPEUTIC LASER LIGHT

308 — RECEIVE RETURN LIGHT

310 — PERFORM SPECTRAL MEASUREMENT

312 — COMPARE TO THRESHOLD

314 — DETERMINE THAT EXCEEDS THRESHOLD

316 — GENERATE FLASHING EVENT DATA SIGNAL

SPECTRAL DETECTION OF OPTICAL FIBER FLASHING EVENT

CROSS-REFERENCE TO RELATED APPLICATION

This application claims the benefit of U.S. Provisional Application No. 63/377,646, filed Sep. 29, 2022, which is hereby incorporated by reference in its entirety.

FIELD OF THE DISCLOSURE

This document relates generally to endoscopic systems, and more specifically relates to systems and methods for determining and controlling a distance between an endoscope tip and a target.

BACKGROUND OF THE DISCLOSURE

An operator, such as a physician, practitioner, or user, can use an endoscope to provide visual access to an internal location of a patient. The operator can insert an endoscope into a patient's body. The endoscope can deliver light to a target being examined, such as a target anatomy or object. The endoscope can collect light that is reflected from the object. The reflected light can carry information about the target being examined.

An endoscope can include a working channel. In some examples, the operator can perform suction through the working channel. In some examples, the operator can pass instruments, such as brushes, biopsy needles or forceps, through the working channel. In some examples, the operator can perform minimally invasive surgery through the working channel, such as to remove unwanted tissue or foreign objects from the body of the patient.

An endoscope can use a laser or plasma system to perform laser therapy, such as ablation, coagulation, vaporization, fragmentation, lithotripsy, and others. In laser therapy, the operator can use the endoscope to deliver surgical laser energy to various target treatment areas, such as soft or hard tissue. In lithotripsy, the operator can use the endoscope to deliver surgical laser energy to break down calculi structures in the patient's kidney, gallbladder, ureter, or other stone-forming regions, or to ablate large calculi into smaller fragments.

SUMMARY

In an example, a laser tissue ablation system can include: an optical fiber including a distal end extendible from an endoscope body of an endoscope, the optical fiber configured to: deliver therapeutic laser light from the distal end of the optical fiber toward a target site; and receive return light into the distal end of the optical fiber; a sensor configured to spectrally measure the return light; and processor circuitry configured to: form a first determination, from the spectral measurement of the return light, whether flashing event light is present in the return light, the flashing event light being generated when a flashing event occurs at the distal end of the optical fiber; and generate, in response to the first determination, a flashing event data signal that indicates whether the flashing event has occurred.

In an example, a method for operating a laser tissue ablation system can include: illuminating, with an illumination light source disposed on a distal end of an endoscope body, a target site with visible light illumination having a visible light illumination spectrum; capturing, with a video camera disposed on the distal end of the endoscope body, a video image of the illuminated target site; delivering therapeutic laser light from a distal end of an optical fiber extending distally from the distal end of the endoscope body toward the target site, the therapeutic laser light having at least one therapeutic laser light wavelength; receiving return light into the distal end of the optical fiber; performing a spectral measurement of the return light to determine a measured light level in a detection spectral region that does not overlap with the visible light illumination spectrum and does not include the at least one therapeutic laser light wavelength; comparing, with processor circuitry, the measured light level to a threshold light level; determining, with the processor circuitry, that the measured light level exceeds the threshold light level; and generating, with the processor circuitry, in response to the determination that the measured light level exceeds the threshold light level, a flashing event data signal that indicates that a flashing event has occurred at the distal end of the optical fiber.

In an example, a laser tissue ablation system can include: an endoscope having an endoscope body; an illumination light source disposed on a distal end of the endoscope body and configured to illuminate a target site with visible light illumination having a visible light illumination spectral range; a video camera disposed on the distal end of the endoscope body and configured to capture a video image of the illuminated target site; a video display configured to display the video image of the illuminated target site; an optical fiber extending from the endoscope body and configured to: deliver therapeutic laser light from a distal end of the optical fiber toward the target site, the therapeutic laser light having at least one therapeutic laser light wavelength; and receive return light into the distal end of the optical fiber; a spectrometer configured to spectrally measure the return light; and processor circuitry configured to: determine, from the spectral measurement of the return light, when a light level of the return light at at least one flashing event wavelength has increased over a threshold light level, the at least one flashing event wavelength being different from the at least one therapeutic laser light wavelength and being outside the visible light illumination spectral range; and generate, in response to a determination that the light level has increased over the threshold light level, a flashing event data signal that indicates that a flashing event has occurred at the distal end of the optical fiber.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

In a laser therapy treatment, a practitioner can position a distal end of an endoscope close to a target, such as a kidney stone. The endoscope can include an optical fiber that can deliver therapeutic laser light to the target, such as via a distal end of the optical fiber. During the treatment, it can be beneficial to dynamically monitor or dynamically control a separation between the distal end of the optical fiber and the target. For example, during a laser tissue ablation procedure, an operator may accidentally bring the distal end of the optical fiber into contact with the tissue while the laser is operational. When such contact occurs while the laser is operational, the contact can produce an event known as flashing. Flashing may not affect an efficacy of tissue ablation, but flashing can degrade or deteriorate the distal end of the optical fiber. Such deterioration can be known as fiber burn back.

Flashing is believed to be caused by burning of organic compounds in the tissue, such as in a stone, such as a kidney stone. Such burning can produce light at wavelengths that are not produced by the laser light source. For example, the laser light sources can produce laser light in a range of wavelength between about 1908 nm and about 2940 nm, or between about 1920 nm and 1960 nm. The light produced by a flashing event can have a wavelength range that peaks at roughly 750 nm, with half-maximum-intensity occurring at about 680 nm and about 840 nm.

The laser tissue ablation system explained in detail below can detect a flashing event, such as by recognizing a spectroscopic profile (e.g., a light intensity as a function of wavelength) of the flashing event. For example, the system can monitor light at one or more wavelengths outside the spectrum of light that is directed toward the tissue. When the light at the one or more wavelengths exceeds a specified threshold value, or increases to exceed to specified threshold value, the system can determine that a flashing event has initiated. As such, when the light level exceeds the specified threshold value, the system can determine that a flashing event is presently occurring.

In response to detecting the flashing event, the system can take one or more actions. For example, the system can reposition the optical fiber such that the distal tip of the optical fiber is further away from the target. Such recognition of the flashing event and repositioning the optical fiber in response to the recognition of the flashing event can increase a longevity of the optical fiber, such as by reducing or eliminating fiber burn back. Other examples can include reducing a power of the laser light source, increasing an irrigation rate at or near the target, suppressing a video image of the target, and others.

Figure 1:
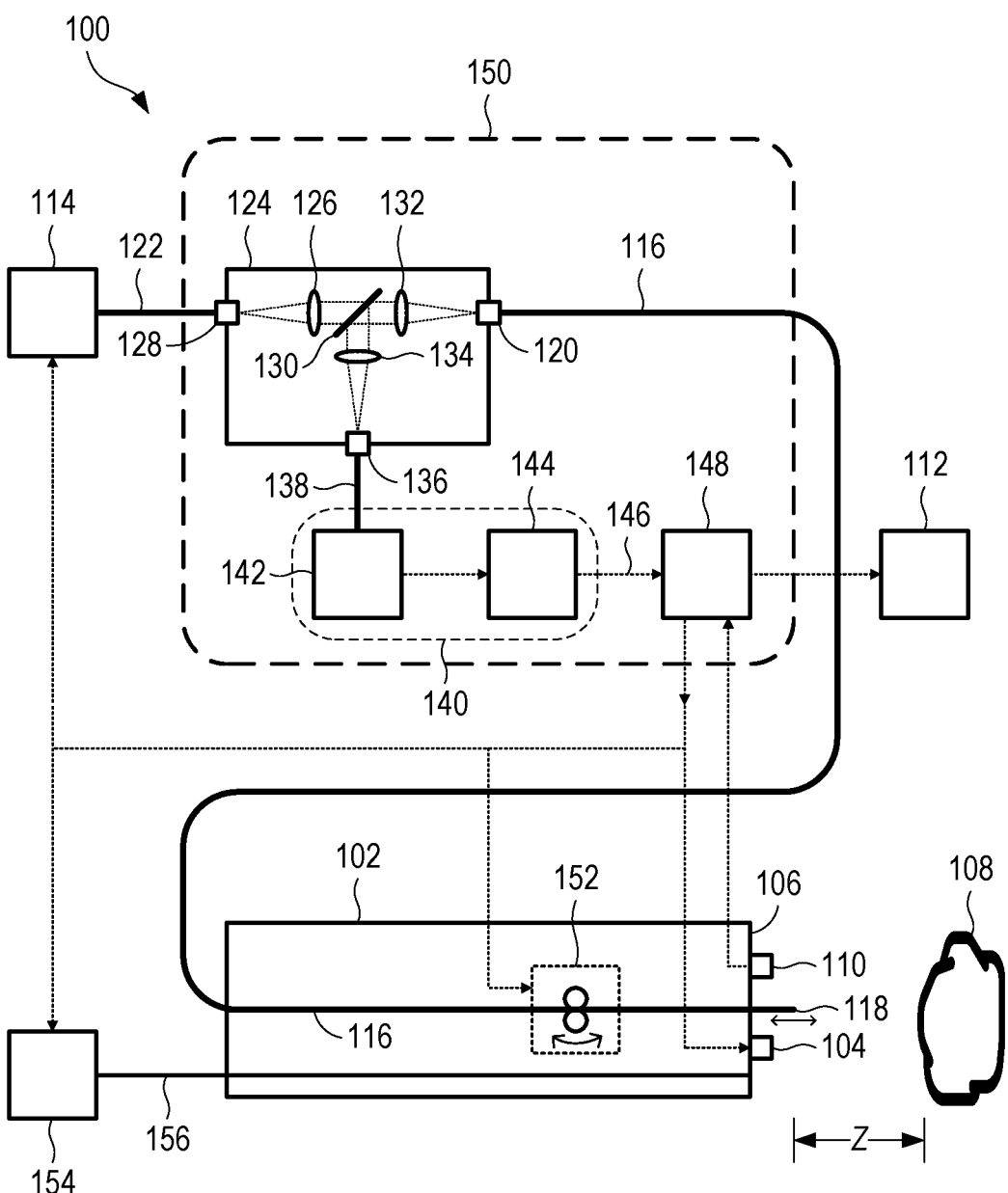
FIG. 1 shows a side-view schematic drawing of an example of a laser tissue ablation system.

FIG. 1 shows a side-view schematic drawing of an example of a laser tissue ablation system 100. The laser tissue ablation system 100 can include an endoscope having an endoscope body 102. The endoscope body 102 can be grippable by the operator, who can position the endoscope body 102 as needed to view and ablate one or more targets, such as kidney stones, in one or more internal locations of the patient. In some examples, the endoscope body 102 can be rigid. In one or more examples, the endoscope body 102 can be elongated along an elongation axis. The endoscope body 102 can include one or more channels, passages, or apertures that extend through the endoscope body 102 along the elongated axis. For example, the endoscope body 102 can include a working channel. In some examples, the operator can perform suction through the working channel. In some examples, the operator can pass instruments, such as brushes, biopsy needles or forceps, through the working channel. In some examples, the operator can perform minimally invasive surgery through the working channel, such as to remove unwanted tissue or foreign objects from the body of the patient. As another example, the endoscope body 102 can include an irrigation channel, which can supply irrigant to the target site, such as to flush away pieces of the target. Other channels can also be used.

The laser tissue ablation system 100 can include an illumination light source 104 disposed on a distal end 106 of the endoscope body 102. For example, the illumination light source 104 can include one or more light emitting diodes disposed on the distal end 106 of the endoscope body 102. In some examples, the light emitting diodes can be white light emitting diodes. For example, a white light emitting diode can include a blue or a violet light emitting diode, coupled with a phosphor that can absorb some or all of the blue or violet light, and in response, can emit light with one or more longer wavelengths, such as in the yellow portion of the electromagnetic spectrum. Other illumination light sources can also be used. The illumination light source 104 can illuminate a target site 108 with visible light illumination having a visible light illumination spectral range. In some examples, the visible light illumination spectral range can include wavelengths in the visible portion of the electromagnetic spectrum.

The laser tissue ablation system 100 can include a video camera 110 disposed on the distal end 106 of the endoscope body 102. In some examples, the video camera 110 can include a lens, a sensor element located at a focal plane of the lens, and electronics that can convert an electrical signal produced by the sensor element into a digital signal. The video camera elements can be located in a relatively small, sealed package at the distal end 106 of the endoscope body 102. The video camera 110 can capture a real-time video image of the illuminated target site 108.

The laser tissue ablation system 100 can include a video display 112 that can display the video image of the illuminated target site 108. For example, the video display 112 can be mounted on or in a rack of equipment, away from the endoscope. The video display 112 can provide a real time image of the target site 108, illuminated with white light from the illumination light source 104, to the practitioner.

The laser tissue ablation system 100 can include a laser light source 114 that can generate laser light, such as in pulsed laser light. The laser light source 114 can be located away from the endoscope body 102, such that the endoscope body 102 can be positionable by the operator, while the laser light source 114 can be disposed in a laser housing that can remain in a fixed position, spaced apart from the endoscope body 102, during a procedure. In some examples, the laser light source 114 can include a thulium fiber laser, which can produce light having one or more wavelengths between about 1920 nm and about 1960 nm. In some examples, the laser light source 114 can include a thulium:YAG (yttrium aluminum garnet) laser, which can produce light at a wavelength of 2010 nm. In some examples, the laser light source 114 can include a holmium:YAG laser, which can produce light at a wavelength of 2120 nm. In some examples, the laser light source 114 can include an erbium:YAG laser, which can produce light at a wavelength of 2940 nm. In some examples, the laser light produced by the laser light source 114 can include a first wavelength, such as a wavelength between about 1908 nm and about 2940 nm, or between about 1920 nm and 1960 nm, between about 1900 nm and about 1940 nm, greater than about 1900 nm, greater than about 1800 nm, or others. For these (and other) laser light sources, the laser light can have a wavelength or wavelengths in a portion of the electromagnetic spectrum at which water (a major component of tissue) has a relatively high absorption. During a procedure, the tissue can absorb the laser light, can heat locally to a relatively high temperature, and can break apart due to local thermal strains within the tissue.

The laser tissue ablation system 100 can include an optical fiber 116 that can extend from the endoscope body 102. In some examples, the optical fiber 116 can be a multi-mode optical fiber. In some examples, the optical fiber 116 can have a distal end 118 that extends from a distal end 106 of the endoscope body 102.

The laser light source 114 can direct laser light into a proximal portion 120 of the optical fiber 116, such as via a laser light source optical fiber 122 and a free-space optical coupler/splitter 124. The free-space optical coupler/splitter 124 can include a collimating lens 126 with a focal plane located at a distal end 128 of the laser light source optical fiber 122, which can collimate (or at least partially focus) light from the laser light source 114. The collimated light can pass through a beamsplitter 130 and be focused by a bi-directional focusing lens 132 onto the proximal portion 120 of the optical fiber 116. The bi-directional focusing lens 132 can collimate the return light that returns through the optical fiber 116. The beamsplitter 130 can direct all or a portion (or a spectral portion) of the return light onto a return-path focusing lens 134, which can focus the return light onto an end 136 of a return-path optical fiber 138. The return-path optical fiber 138 can direct the return light to a sensor (described below). The free-space optical coupler/splitter 124 is but one configuration for such a coupler/splitter. Alternatively, a fiber-based optical coupler/splitter can also be used.

The optical fiber 116 can direct the laser light distally along a length of the optical fiber 116 to emerge from the distal end 118 of the optical fiber 116 to form therapeutic laser light. The optical fiber 116 can deliver the therapeutic laser light from the distal end 118 of the optical fiber 116 toward a target site 108. The therapeutic laser light can include at least one therapeutic laser light wavelength, such as a wavelength between about 1908 nm and about 2940 nm, or between about 1920 nm and 1960 nm, between about 1900 nm and about 1940 nm, greater than about 1900 nm, greater than about 1800 nm, or other suitable value or values.

The optical fiber 116 can receive return light into the distal end 118 of the optical fiber 116. In some examples, the return light can include at least some of the therapeutic laser light that is reflected from the target site 108. When a flashing event occurs, the return light can additionally include flashing event light. The flashing event light can have a spectral profile that differs from that of the therapeutic laser light. In other words, the flashing event light can be spectrally separate from the therapeutic laser light. For example, the flashing event light can have a spectral profile that peaks at roughly 750 nm, with light intensities at half-maximum at about 680 nm and about 840 nm. In some examples, the flashing event light can have a spectral profile that includes wavelengths that are less than one or more wavelengths of the therapeutic laser light.

The laser tissue ablation system 100 can include a sensor 140 that can spectrally measure the return light. For example, the sensor 140 can measure the return light at one or more specified wavelengths or wavelength regions. The specified wavelength or wavelength regions may be absent from a spectrum of the illumination light and may differ from the one or more wavelengths of the therapeutic laser light. In other words, the sensor 140 can measure the return light at one or more wavelengths that are not directed toward the target site 108 from the endoscope. In some examples, the sensor 140 can filter out one or more wavelength regions and can detect one or more of the remaining wavelength regions that are not filtered out.

The sensor 140 can include a light-sensitive sensor element 142, which can convert an optical signal, such as the return light, into an internal electrical signal. The sensor 140, as shown in the configuration of FIG. 1, can also include sensor circuitry 144, which can convert or process the internal electrical signal from the light-sensitive sensor element 142 into an analog or digital sensor data signal 146 that can be interpreted by the processor circuitry 148 (described below). The sensor 140 can further include one or more wavelength-sensitive elements, which can allow the sensor circuitry 144 to provide intensity measurements of the return light, as a function of wavelength.

For example, the wavelength-sensitive element of the sensor 140 can include a dichroic beamsplitter (e.g., implemented as a thin-film coating on the beamsplitter 130) that can separate the flashing event light (for example, with wavelengths between about 680 nm and about 840 nm) from the therapeutic laser light (for example, with one or more wavelengths between about 1900 nm and about 1940 nm). The dichroic beamsplitter can have a threshold wavelength, can direct light with wavelengths less than the threshold wavelength along a first optical path, and can direct light with wavelengths greater than the threshold wavelength along a second optical path. The threshold wavelength can have any suitable wavelength value between a spectral profile of the flashing event light and a wavelength of the therapeutic laser light. For example, the threshold wavelength may be 1000 nm, 1500 nm, 1700 nm, or any other suitable value. In some examples, the dichroic beamsplitter can be implemented as a thin-film coating on a surface of a transparent optical element, such as a prism.

In some configurations, the sensor 140 can include a dichroic beamsplitter (e.g., implemented as a thin-film coating on the beamsplitter 130) that can receive the return light, direct the therapeutic laser light along a first optical path, and direct the flashing event light along a second optical path. The light-sensitive sensor element 142 of the sensor 140 can include a sensor element or detector that can detect light from the second optical path. Such a sensor can detect a flash event as a presence (or an increase) of a signal produced by the sensor 140. In some examples, the light-sensitive sensor element 142 can include a single detector element. In other examples, the light-sensitive sensor element 142 can include a multi-pixel detector element. The sensor 140 can further include sensor circuitry 144, which can produce one or more sensor data signals 146 in response to light received by the light sensor. The processor circuitry 148 (described below) can analyze the one or more sensor data signals 146 to determine if and/or when a flashing event has occurred.

In some configurations, the sensor circuitry 144 of the sensor 140 (and, optionally, the wavelength-sensitive element of the sensor 140) can include a spectrometer that can spectrally measure the return light. For these configurations, the light-sensitive sensor element 142 can include a spectrometer sensor or spectrometer detector, which can receive all or a portion of the return light. For these configurations, the sensor data signal 146 can be a spectrometer output signal that includes data that represents light intensity (or amplitude, or other suitable photometric quantity) as a function of wavelength. The processor circuitry 148 (described below) can analyze the spectrometer output signal to determine if and/or when a flashing event has occurred.

For configurations in which the sensor 140 includes a spectrometer, the laser tissue ablation system 100 can optionally perform analysis of the target, based on the return light. For example, the spectrometer and the processor circuitry 148 can use the flashing event light to generate a spectral profile of the target site 108. In some examples, the processor circuitry 148 (described below) can use the spectral profile of the target site 108 to determine a material composition of the target site 108, such as by matching the measured spectral profile of the target site 108 to one or more of a specified (finite) plurality of predetermined spectral profiles that correspond to known materials. These are but examples; other suitable analyses of the target site 108 can also be performed.

The laser tissue ablation system 100 can include processor circuitry. In some examples, the processor circuitry 148 may be referred to as a controller. In some examples, the processor circuitry 148 may be implemented purely in software. In some examples, the processor circuitry 148 may be implemented purely in hardware. In some examples, the processor circuitry 148 may be implemented as a combination of software and hardware. In some examples, the processor circuitry 148 may be implemented on a single processor. In some examples, the processor circuitry 148 may be implemented on multiple processors. In some examples, the multiple processors may be housed in a common housing. In some examples, at least two of the multiple processors may be spaced apart in different housings.

The processor circuitry 148 can analyze one or more signals produced by the sensor 140, such as the sensor data signal 146 or the spectrometer output signal, to determine if and/or when a flashing event has occurred.

For example, the processor circuitry 148 can form a first determination, from the spectral measurement of the return light, whether flashing event light is present in the return light. The flashing event light can be generated when a flashing event occurs at the distal end 118 of the optical fiber 116. The processor circuitry 148 can generate, in response to the first determination, a flashing event data signal that indicates whether the flashing event has occurred.

As another example, in which the spectral measurement of the return light has determined a measured light level in a detection spectral region that does not overlap with the visible light illumination spectrum and does not include the at least one therapeutic laser light wavelength, the processor circuitry 148 can compare the measured light level to a threshold light level, such as a value saved on a server or in a lookup table. The processor circuitry 148 can determine if and/or when the measured light level exceeds the threshold light level. In response to a determination that the measured light level exceeds the threshold light level, the processor circuitry 148 can generate a flashing event data signal that indicates that a flashing event has occurred at the distal end 118 of the optical fiber 116.

As another example, the processor circuitry 148 can determine, from the spectral measurement of the return light, when a light level of the return light at at least one flashing event wavelength has increased over a threshold light level. The at least one flashing event wavelength can be different from the at least one therapeutic laser light wavelength and can be outside the visible light illumination spectral range. In response to a determination that the light level has increased over the threshold light level, the processor circuitry 148 can generate a flashing event data signal that indicates that a flashing event has occurred at the distal end 118 of the optical fiber 116.

In some examples, the threshold light level can be a constant over time (e.g., invariant). In some examples, the threshold light level can vary over time, such as varying with an output power of the laser light source 114. The processor circuitry 148 can use other suitable signal analysis techniques to determine that a flashing event has occurred.

In some examples, the free-space optical coupler/splitter 124, the sensor 140, and the processing circuitry 148 can be included in a housing 150. The laser light source 114 can direct laser light into the housing via the laser light source optical fiber 122. The optical fiber 116 can direct the laser light from the housing 150 to the endoscope body 102 and can tether the endoscope to the housing 150. The video display 112 can optionally be attached to the housing 150 or made integral with the housing 150.

When the processor circuitry 148 has determined that a flashing event has occurred, the processor circuitry 148 can cause an action to occur. For example, in response to the first determination (e.g., a determination that a flashing event has occurred), the processor circuitry 148 can generate a flashing event data signal that indicates whether the flashing event has occurred. In some examples, the flashing event data signal can be an electrical signal. For example, the flashing event data signal can have a first voltage when there is no flashing event and can have a second voltage when a flashing event has occurred. In some examples, the flashing event data signal can be a digital signal. For example, the flashing event data signal can include a variable, stored in memory. The variable can have a first value when there is no flashing event and can have a second value when a flashing event has occurred. Other suitable flashing event data signals can also be used.

An example of an action (taken in response to determining that a flashing event has occurred) is causing the optical fiber 116 to retract proximally in order to terminate the flashing event (e.g., to increase the distance (Z) in FIG. 1). For example, the laser tissue ablation system 100 can further include an actuator 152 that can automatically retract the optical fiber 116 proximally with respect to the endoscope body 102 in response to receiving data that corresponds to the flashing event data signal. In some examples, such as the configuration of FIG. 1, the actuator 152 can include a wheel. The wheel can have a center that is fixed in position with respect to the endoscope body 102. The wheel can have a circumferential surface that contacts the optical fiber 116. The wheel can be rotatable from a rotary actuator, such as a rotary actuator disposed at or near the center of the wheel. In some examples, the actuator 152 can automatically retract the optical fiber 116 proximally with respect to the endoscope body 102 by a specified distance in response to receiving the data that corresponds to the flashing event data signal. The specified distance can be sufficient to terminate the flashing event, such as 1 mm, about 1 mm, or any other suitable value. The actuator 152 described above and shown in FIG. 1 is but one example of an actuator that can proximally retract the optical fiber 116 to terminate the flashing event. Other suitable actuators can also be used.

Another example of an action (taken in response to determining that the flashing event has occurred) is to cause the laser light source 114 to reduce its output power, optionally to zero.

Another example of an action (taken in response to determining that the flashing event has occurred) is to supply more irrigant to the target site 108. For example, the laser tissue ablation system 100 can include an irrigation regulator 154 coupled to the endoscope. The irrigation regulator 154 can supply an irrigant, such as a saline solution, to the target site 108, via an irrigation line 156, at a controllable irrigation rate. The processor circuitry 148 can cause the irrigation regulator 154 to increase the irrigation rate in response to receiving data that corresponds to the flashing event data signal.

Another example of an action (taken in response to determining that the flashing event has occurred) is to suppress or interrupt a displayed video image of the target site 108. For example, the laser tissue ablation system 100 can include an illumination light source 104 disposed on a distal end 106 of the endoscope body 102. The illumination light source 104 can illuminate the target site 108 with visible illumination. The laser tissue ablation system 100 can include a video camera 110 disposed on the distal end 106 of the endoscope body 102. The video camera 110 can capture a video image of the illuminated target site 108. The laser tissue ablation system 100 can include a video display 112 coupled to the processor circuitry 148. The video display 112 can display the video image of the illuminated target site 108. The processor circuitry 148 can suppress the video image in response to receiving data that corresponds to the flashing event data signal, such that the video display 112 does not display the video image when the flashing event is occurring. The examples of actions taken in response to determining that the flashing event has occurred are but mere examples; the processing circuitry can alternatively cause other suitable actions to be taken.

In some examples, the processor circuitry 148 can optionally determine when or if the flashing event has ceased and can optionally take an additional action in response to determining that the flashing event has ceased. For example, the processor circuitry 148 can form a second determination, from spectral measurement of the return light that indicates that the flashing event light is no longer present in the return light, that the flashing event has ceased. The processor circuitry 148 can resume displaying the video image on the video display 112, in response to forming the second determination. Other suitable actions can also be taken, such as causing the laser light source 114 to increase its output power, optionally to a previous output power level that was utilized before the processor circuitry 148 determined that the flashing event was occurring.

In some examples, the processor circuitry 148 may take action after the processor circuitry 148 has detected a specified number of flashing events within a specified time interval. In some examples, the processor circuitry 148 may take action after the processor circuitry 148 has detected a specified number of flashing events in a specified number of sequential laser pulses. Other criteria can also be used.

Figure 2:
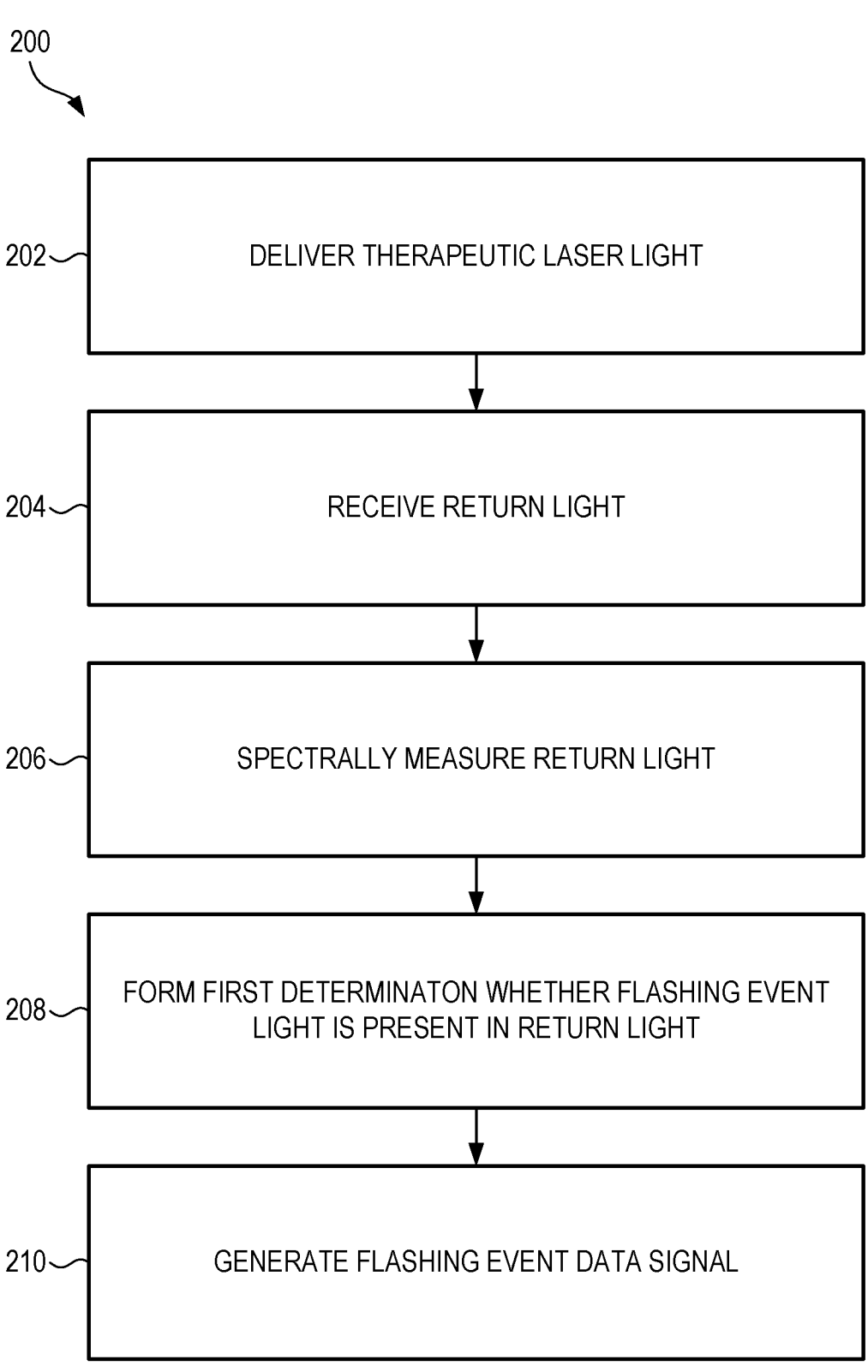
FIG. 2 shows a flow chart of an example of a method for operating a laser tissue ablation system.

FIG. 2 shows a flow chart of an example of a method 200 for operating a laser tissue ablation system, such as the laser tissue ablation system 100 of FIG. 1, or any other suitable laser tissue ablation system. The method 200 is but one example of a method for operating a laser tissue ablation system; other methods can also be used.

At operation 202, an optical fiber, including a distal end extendible from an endoscope body of an endoscope, can deliver therapeutic laser light from the distal end of the optical fiber toward a target site.

At operation 204, the optical fiber can receive return light into the distal end of the optical fiber.

At operation 206, a sensor can spectrally measure the return light.

At operation 208, processor circuitry can form a first determination, from the spectral measurement of the return light, whether flashing event light is present in the return light. The flashing event light can be generated when a flashing event occurs at the distal end of the optical fiber.

At operation 210, the processor circuitry can generate, in response to the first determination, a flashing event data signal that indicates whether the flashing event has occurred.

Figure 3:
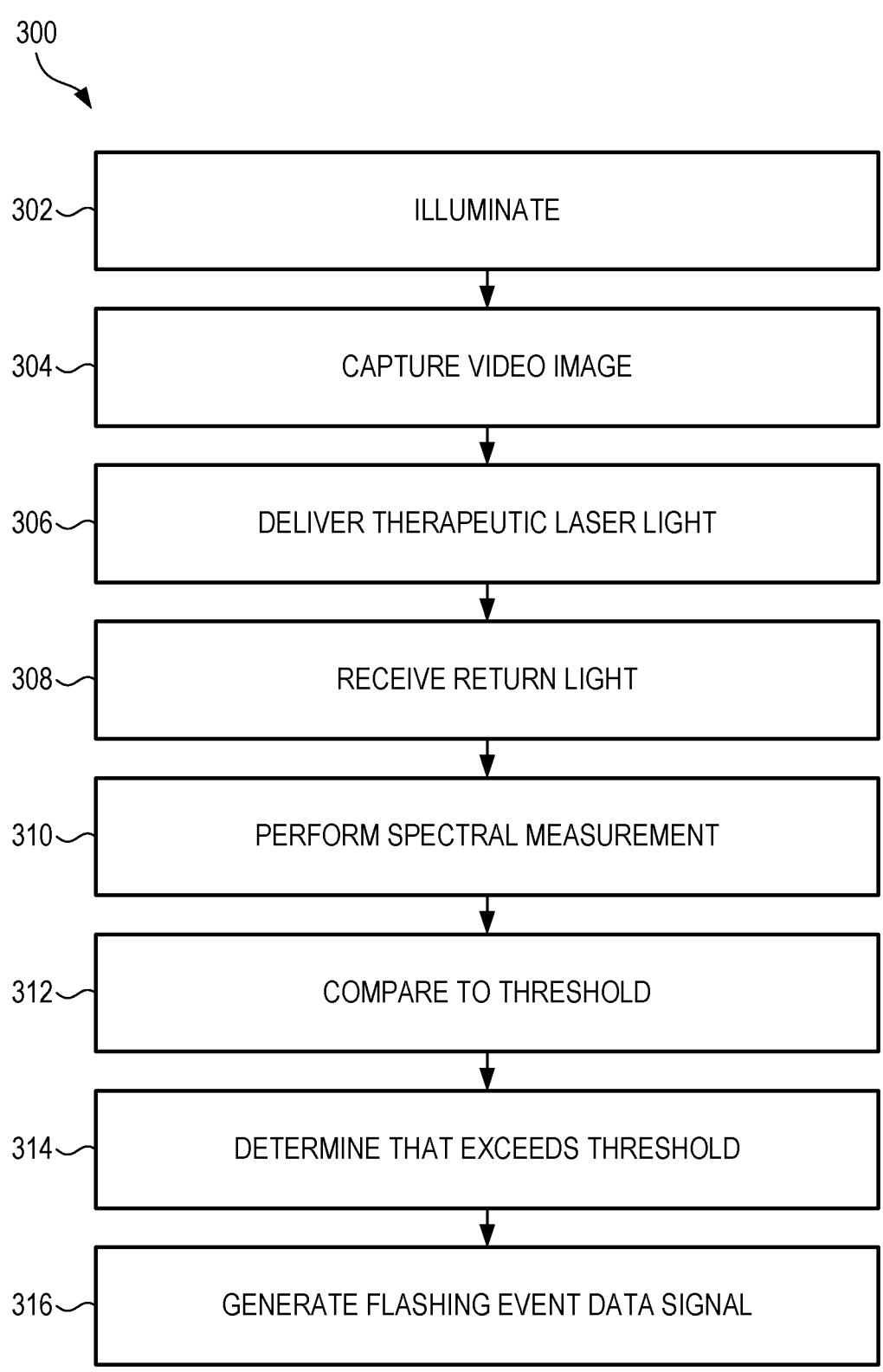
FIG. 3 shows a flow chart of an example of a method for operating a laser tissue ablation system.

FIG. 3 shows a flow chart of an example of a method 300 for operating a laser tissue ablation system, such as the laser tissue ablation system 100 of FIG. 1, or any other suitable laser tissue ablation system. The method 300 is but one example of a method for operating a laser tissue ablation system; other methods can also be used.

At operation 302, an illumination light source disposed on a distal end of an endoscope body can illuminate a target site with visible light illumination having a visible light illumination spectrum.

At operation 304, a video camera disposed on the distal end of the endoscope body can capture a video image of the illuminated target site.

At operation 306, an optical fiber, extending distally from the distal end of the endoscope body, can deliver therapeutic laser light from a distal end of an optical fiber toward the target site. The therapeutic laser light can have at least one therapeutic laser light wavelength.

At operation 308, an optical fiber can receive return light into the distal end of the optical fiber.

At operation 310, the laser tissue ablation system can perform a spectral measurement of the return light to determine a measured light level in a detection spectral region that does not overlap with the visible light illumination spectrum and does not include the at least one therapeutic laser light wavelength.

At operation 312, processor circuitry can compare the measured light level to a threshold light level.

At operation 314, the processor circuitry can determine that the measured light level exceeds the threshold light level.

At operation 316, the processor circuitry can generate, in response to the determination that the measured light level exceeds the threshold light level, a flashing event data signal that indicates that a flashing event has occurred at the distal end of the optical fiber.

In some examples, the method 300 can optionally further include causing, with the processor circuitry, an actuator to retract the optical fiber proximally with respect to the endoscope body by a specified distance in response to the determination that the measured light level exceeds the threshold light level, the specified distance being sufficient to terminate the flashing event.

In some examples, the method 300 can optionally further include displaying, on a video display coupled to the processor circuitry, the video image of the illuminated target site; and suppressing, with the processor circuitry, the video image in response to the determination that the measured light level exceeds the threshold light level, such that the video display does not display the video image when the flashing event is occurring.

In some examples, the method 300 can optionally further include supplying, with an irrigation regulator coupled to the endoscope, an irrigant to the target site at a controllable irrigation rate; and increasing, with the irrigation regulator, the irrigation rate in response to the determination that the measured light level exceeds the threshold light level.

Figure 4:
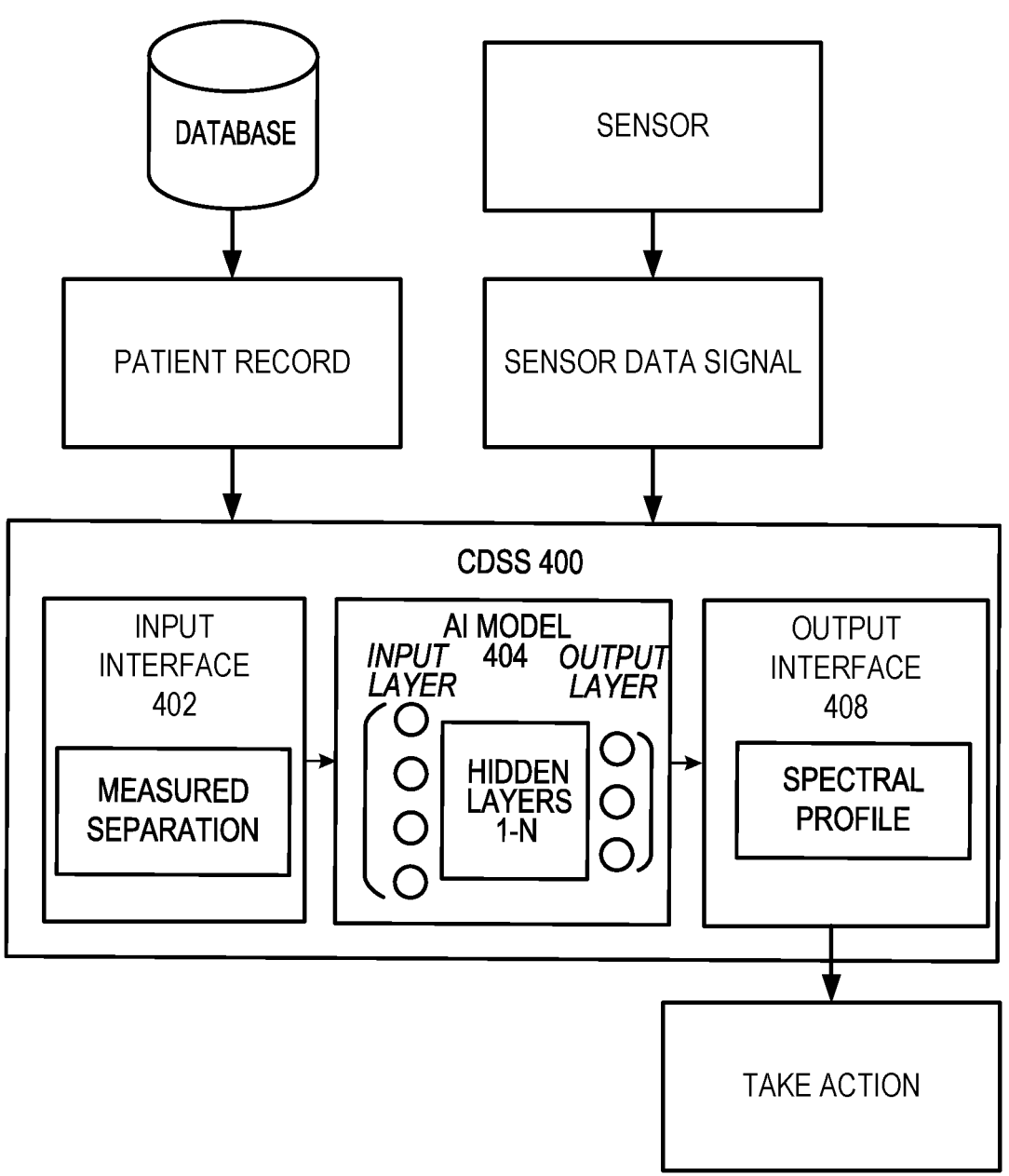
FIG. 4 shows a schematic diagram of an exemplary computer-based clinical decision support system (CDSS) that is configured to determine if or when a flashing event is occurring at the distal end of the optical fiber, and, in response, take a suitable action, such as proximally retract the optical fiber to cease the flashing event.

FIG. 4 shows a schematic diagram of an exemplary computer-based clinical decision support system (CDSS) 400 that is configured to determine if or when a flashing event is occurring at the distal end of the optical fiber, and, in response, take a suitable action, such as proximally retract the optical fiber to cease the flashing event. In various embodiments, the CDSS 400 includes an input interface 402 through which the sensor data signal 146 can be provided as input features to an artificial intelligence (AI) model 404, a processor such as a controller or processor circuitry 148 which performs an inference operation in which the determination if and/or when a flashing event has occurred is communicated to a user, e.g., a clinician.

In some embodiments, the input interface 402 may be a direct data link between the CDSS 400 and one or more medical devices, such as laser tissue ablation system 100 or endoscope, which generate at least some of the input features. For example, the input interface 402 may transmit the determination directly to the CDSS during a therapeutic and/or diagnostic medical procedure. Additionally, or alternatively, the input interface 402 may be a classical user interface that facilitates interaction between a user and the CDSS 400. For example, the input interface 402 may facilitate a user interface through which the user may manually enter the determination. Additionally, or alternatively, the input interface 402 may provide the CDSS 400 with access to an electronic patient record from which one or more input features may be extracted. In any of these cases, the input interface 402 is configured to collect the determination in association with a specific patient on or before a time at which the CDSS 400 is used to assess the medical condition addressed by the laser tissue ablation system 100 or endoscope, such as a kidney stone.

Based on one or more of the above input features, the controller or processor circuitry 148 performs an inference operation using the AI model to generate the determination. For example, input interface 402 may deliver the sensor data signal 146 tinto an input layer of the AI model which propagates this input feature through the AI model to an output layer. The AI model can provide a computer system the ability to perform tasks, without explicitly being programmed, by making inferences based on patterns found in the analysis of data. AI model explores the study and construction of algorithms (e.g., machine-learning algorithms) that may learn from existing data and make predictions about new data. Such algorithms operate by building an AI model from example training data in order to make data-driven predictions or decisions expressed as outputs or assessments.

There are two common modes for machine learning (ML): supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled and allowing the algorithm to act on that information without guidance. Unsupervised ML is useful in exploratory analysis because it can automatically identify structure in data.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model may be trained continuously or periodically prior to performance of the inference operation by the controller or processor circuitry 148. Then, during the inference operation, the patient specific input features provided to the AI model may be propagated from an input layer, through one or more hidden layers, and ultimately to an output layer that corresponds to the value of distance (Z).

In some examples, the AI model can include a database, which can include data corresponding to a patient. The database can provide a patient record to the CDSS 400. IN some examples, the AI model can receive a sensor data signal 146 from a sensor, such as sensor 140.

During and/or subsequent to the inference operation, the determination may be communicated to the user via the user interface (UI) and/or automatically cause an actuator or an alarm connected to the processor to perform a desired action. For example, the controller or processor circuitry 148 can cause the actuator to move the optical fiber with respect to the endoscope. Alternatively, the controller or processor circuitry 148 can cause an alarm to alert the practitioner.

In some examples, the CDSS 400 can optionally be used to determine the action taken in response to a sensor data signal 146.

Some features as described herein may provide methods and apparatus that can identify the composition of various targets, for instance, in medical applications (e.g., soft or hard tissue) in vivo through an endoscope. This may allow the operator to continuously monitor the composition of the target viewed through the endoscope throughout the procedure. This also can be used in combination with a laser system where the method may send feedback to the laser system to adjust the settings based on the composition of the target. This feature may allow for the instant adjustment of laser settings within a set range of the original laser setting selected by the operator.

Some features as described herein may be used to provide a system and method that measures differences, such as the chemical composition of a target, in vivo and suggests laser settings or automatically adjusts laser settings to better achieve a desired effect. Examples of targets and applications include laser lithotripsy of renal calculi and laser incision or vaporization of soft tissue. In one example, three major components are provided: the laser, the spectroscopy system, and the feedback analyzer. In an example, a controller of the laser system may automatically program laser therapy with appropriate laser parameter settings based on target composition. In an example, the laser may be controlled based on a machine learning algorithm trained with spectroscope data. Additionally or alternatively, an operator may receive an indication of target type continuously during the procedure, and be prompted to adjust the laser setting. By adjusting laser settings and adapting the laser therapy to composition portions of a single calculus target, stone ablation or dusting procedures can be performed faster and in a more energy-efficient manner.

Some features as described herein may provide systems and methods for providing data inputs to the feedback analyzer to include internet connectivity, and connectivity to other surgical devices with a measuring function. Additionally, the laser system may provide input data to another system such as an image processor whereby the procedure monitor may display information to the operator relevant to the medical procedure. One example of this is to identify different soft tissues more clearly in the field of view during a procedure, vasculature, capsular tissue, and different chemical compositions in the same target, such as a stone for example.

Some features as described herein may provide systems and methods for identifying different target types, such as different tissue types, or different calculus types. In some cases, a single calculus structure (e.g., a kidney, bladder, pancreobiliary, or gallbladder stone) may have two or more different compositions throughout its volume, such as brushite, calcium phosphate (CaP), dihydrate calcium oxalate (COD), monohydrate calcium oxalate (COM), magnesium ammonium phosphate (MAP), or a cholesterol-based or a uric acid-based calculus structure. For example, a target calculus structure may include a first portion of COD and a second portion of COM. According to one aspect, the present document describes a system and a method for continuously identifying different compositions contained in a single target (e.g., a single stone) based on continuous collection and analysis of spectroscopic data in vivo. The treatment (e.g., laser therapy) may be adapted in accordance with the identified target composition. For example, in response to an identification of a first composition (e.g., COD) in a target stone, the laser system may be programmed with a first laser parameter setting (e.g., power, exposure time, or firing angle, etc.) and deliver laser beams accordingly to ablate or dust the first portion. Spectroscopic data may be continuously collected and analyzed during the laser therapy. In response to an identification of a second composition (e.g., COM) different than the first composition in the same target stone being treated, the laser therapy may be adjusted such as by programing the laser system with a second laser parameter setting different from the laser parameter setting (e.g., different power, or exposure time, or firing angle, etc.), and delivering laser beams accordingly to ablate or dust the second portion of the same target stone. In some examples, multiple different laser sources may be included in the laser system. Stone portions of different compositions may be treated by different laser sources. The appropriate laser to use may be determined by the identification of stone type.

Some features as described herein may be used in relation to a laser system for various applications where it may be advantageous to incorporate different types of laser sources. For instance, the features described herein may be suitable in industrial or medical settings, such as medical diagnostic, therapeutic and surgical procedures. Features as described herein may be used regarding an endoscope, laser surgery, laser lithotripsy, laser settings, and/or spectroscopy.

In the foregoing detailed description, the method and apparatus of the present disclosure have been described with reference to specific embodiments thereof. It will, however, be evident that various modifications and changes may be made thereto without departing from the broader spirit and scope of the present disclosure. The present specification and figures are accordingly to be regarded as illustrative rather than restrictive.

To further illustrate the device and related method disclosed herein, a non-limiting list of examples is provided below. Each of the following non limiting examples can stand on its own or can be combined in any permutation or combination with any one or more of the other examples.

In Example 1, a laser tissue ablation system can comprise: an optical fiber including a distal end extendible from an endoscope body of an endoscope, the optical fiber configured to: deliver therapeutic laser light from the distal end of the optical fiber toward a target site; and receive return light into the distal end of the optical fiber; a sensor configured to spectrally measure the return light; and processor circuitry configured to: form a first determination, from the spectral measurement of the return light, whether flashing event light is present in the return light, the flashing event light being generated when a flashing event occurs at the distal end of the optical fiber; and generate, in response to the first determination, a flashing event data signal that indicates whether the flashing event has occurred.

In Example 2, the laser tissue ablation system of Example 1 can optionally be configured such that the flashing event light is spectrally separated from the therapeutic laser light.

In Example 3, the laser tissue ablation system of any one of Examples 1-2 can optionally be configured such that: the therapeutic laser light includes a first wavelength; and the flashing event light has a spectral profile that includes wavelengths that are less than the first wavelength.

In Example 4, the laser tissue ablation system of any one of Examples 1-3 can optionally further comprise: an actuator controllable by the processor circuitry, the actuator configured to automatically retract the optical fiber proximally with respect to the endoscope body by a specified distance in response to the first determination, the specified distance being sufficient to terminate the flashing event.

In Example 5, the laser tissue ablation system of any one of Examples 1-4 can optionally be configured such that the actuator comprises a wheel, the wheel having a center that is fixed in position with respect to the endoscope body, the wheel having a circumferential surface that contacts the optical fiber, the wheel being rotatable from a rotary actuator controllable by the processor circuitry.

In Example 6, the laser tissue ablation system of any one of Examples 1-5 can optionally further comprise: an illumination light source disposed on a distal end of the endoscope body and configured to illuminate the target site with visible illumination; a video camera disposed on the distal end of the endoscope body and configured to capture a video image of the illuminated target site; and a video display coupled to the processor circuitry and configured to display the video image of the illuminated target site, the processor circuitry being further configured to suppress the video image in response to the first determination, such that the video display does not display the video image when the flashing event is occurring.

In Example 7, the laser tissue ablation system of any one of Examples 1-6 can optionally be configured such that the processor circuitry is further configured to: form a second determination, from spectral measurement of the return light that indicates that the flashing event light is no longer present in the return light, that the flashing event has ceased; and resume displaying the video image on the video display, in response to forming the second determination.

In Example 8, the laser tissue ablation system of any one of Examples 1-7 can optionally further comprise an irrigation regulator coupled to the endoscope and configured to supply an irrigant to the target site at a controllable irrigation rate, the irrigation regulator being further configured to increase the irrigation rate in response to receiving data that corresponds to the flashing event data signal.

In Example 9, the laser tissue ablation system of any one of Examples 1-8 can optionally be configured such that the sensor comprises a spectrometer.

In Example 10, the laser tissue ablation system of any one of Examples 1-9 can optionally be configured such that the spectrometer and the processor circuitry are further configured to use the flashing event light to generate a spectral profile of the target site.

In Example 11, the laser tissue ablation system of any one of Examples 1-10 can optionally be configured such that the processor circuitry is further configured to use the spectral profile of the target site to determine a material composition of the target site.

In Example 12, the laser tissue ablation system of any one of Examples 1-11 can optionally be configured such that the sensor comprises: a dichroic beamsplitter configured to receive the return light, direct the therapeutic laser light along a first optical path, and direct the flashing event light along a second optical path; and a light sensor configured to detect light from the second optical path.

In Example 13, a method for operating a laser tissue ablation system can comprise: illuminating, with an illumination light source disposed on a distal end of an endoscope body, a target site with visible light illumination having a visible light illumination spectrum; capturing, with a video camera disposed on the distal end of the endoscope body, a video image of the illuminated target site; delivering therapeutic laser light from a distal end of an optical fiber extending distally from the distal end of the endoscope body toward the target site, the therapeutic laser light having at least one therapeutic laser light wavelength; receiving return light into the distal end of the optical fiber; performing a spectral measurement of the return light to determine a measured light level in a detection spectral region that does not overlap with the visible light illumination spectrum and does not include the at least one therapeutic laser light wavelength; comparing, with processor circuitry, the measured light level to a threshold light level; determining, with the processor circuitry, that the measured light level exceeds the threshold light level; and generating, with the processor circuitry, in response to the determination that the measured light level exceeds the threshold light level, a flashing event data signal that indicates that a flashing event has occurred at the distal end of the optical fiber.

In Example 14, the method of Example 13 can optionally further comprise: causing, with the processor circuitry, an actuator to retract the optical fiber proximally with respect to the endoscope body by a specified distance in response to the determination that the measured light level exceeds the threshold light level, the specified distance being sufficient to terminate the flashing event.

In Example 15, the method of anyone of Examples 13-14 can optionally further comprise: displaying, on a video display coupled to the processor circuitry, the video image of the illuminated target site; and suppressing, with the processor circuitry, the video image in response to the determination that the measured light level exceeds the threshold light level, such that the video display does not display the video image when the flashing event is occurring.

In Example 16, the method of anyone of Examples 13-15 can optionally further comprise: supplying, with an irrigation regulator coupled to the endoscope, an irrigant to the target site at a controllable irrigation rate; and increasing, with the irrigation regulator, the irrigation rate in response to the determination that the measured light level exceeds the threshold light level.

In Example 17, a laser tissue ablation system can comprise: an endoscope having an endoscope body; an illumination light source disposed on a distal end of the endoscope body and configured to illuminate a target site with visible light illumination having a visible light illumination spectral range; a video camera disposed on the distal end of the endoscope body and configured to capture a video image of the illuminated target site; a video display configured to display the video image of the illuminated target site; an optical fiber extending from the endoscope body and configured to: deliver therapeutic laser light from a distal end of the optical fiber toward the target site, the therapeutic laser light having at least one therapeutic laser light wavelength; and receive return light into the distal end of the optical fiber; a spectrometer configured to spectrally measure the return light; and processor circuitry configured to: determine, from the spectral measurement of the return light, when a light level of the return light at at least one flashing event wavelength has increased over a threshold light level, the at least one flashing event wavelength being different from the at least one therapeutic laser light wavelength and being outside the visible light illumination spectral range; and generate, in response to a determination that the light level has increased over the threshold light level, a flashing event data signal that indicates that a flashing event has occurred at the distal end of the optical fiber.

In Example 18, the laser tissue ablation system of Example 17 can optionally further comprise: an actuator controllable by the processor circuitry, the actuator configured to automatically retract the optical fiber proximally with respect to the endoscope body by a specified distance in response to the determination that the light level has increased over the threshold light level, the specified distance being sufficient to terminate the flashing event.

In Example 19, the laser tissue ablation system of any one of Examples 17-18 can optionally be configured such that the processor circuitry is further configured to suppress the video image in response to the determination that the light level has increased over the threshold light level, such that the video display does not display the video image when the flashing event is occurring.

In Example 20, the laser tissue ablation system of any one of Examples 17-19 can optionally further comprise an irrigation regulator coupled to the endoscope and configured to supply an irrigant to the target site at a controllable irrigation rate, the processor circuitry being further configured to increase the irrigation rate in response to the determination that the light level has increased over the threshold light level.

What is claimed is:

1. A laser tissue ablation system, comprising:
an optical fiber including a distal end extendible from an endoscope body of an endoscope, the optical fiber configured to:
deliver therapeutic laser light from the distal end of the optical fiber toward a target site; and receive return light into the distal end of the optical fiber;

a sensor configured to spectrally measure the return light;

processor circuitry configured to:

form a first determination, from the spectral measurement of the return light, whether flashing event light is present in the return light, the flashing event light being generated when a flashing event occurs at the distal end of the optical fiber; and generate, in response to the first determination, a flashing event data signal that indicates whether the flashing event has occurred; and an actuator controllable by the processor circuitry, the actuator configured to automatically retract the optical fiber proximally with respect to the endoscope body by a specified distance in response to the first determination, the specified distance being sufficient to terminate the flashing event.

2. The laser tissue ablation system of claim 1, wherein the flashing event light is spectrally separated from the therapeutic laser light.

3. The laser tissue ablation system of claim 1, wherein:

the therapeutic laser light includes a first wavelength; and the flashing event light has a spectral profile that includes wavelengths that are less than the first wavelength.

4. The laser tissue ablation system of claim 1, wherein the actuator comprises a wheel, the wheel having a center that is fixed in position with respect to the endoscope body, the wheel having a circumferential surface that contacts the optical fiber, the wheel being rotatable from a rotary actuator controllable by the processor circuitry.

5. The laser tissue ablation system of claim 1, further comprising an irrigation regulator coupled to the endoscope and configured to supply an irrigant to the target site at a controllable irrigation rate, the irrigation regulator being further configured to increase the irrigation rate in response to receiving data that corresponds to the flashing event data signal.

6. The laser tissue ablation system of claim 1, wherein the sensor comprises a spectrometer.

7. The laser tissue ablation system of claim 6, wherein the spectrometer and the processor circuitry are further configured to use the flashing event light to generate a spectral profile of the target site.

8. The laser tissue ablation system of claim 7, wherein the processor circuitry is further configured to use the spectral profile of the target site to determine a material composition of the target site.

9. The laser tissue ablation system of claim 1, wherein the sensor comprises:

a dichroic beamsplitter configured to receive the return light, direct the therapeutic laser light along a first optical path, and direct the flashing event light along a second optical path; and a light sensor configured to detect light from the second optical path.

10. A laser tissue ablation system, comprising:

an optical fiber including a distal end extendible from an endoscope body of an endoscope, the optical fiber configured to:

deliver therapeutic laser light from the distal end of the optical fiber toward a target site; and receive return light into the distal end of the optical fiber;

a sensor configured to spectrally measure the return light;

processor circuitry configured to:

form a first determination, from the spectral measurement of the return light, whether flashing event light is present in the return light, the flashing event light being generated when a flashing event occurs at the distal end of the optical fiber; and generate, in response to the first determination, a flashing event data signal that indicates whether the flashing event has occurred;

an illumination light source disposed on a distal end of the endoscope body and configured to illuminate the target site with visible illumination to create an illuminated target site;

a video camera disposed on the distal end of the endoscope body and configured to capture a video image of the illuminated target site; and a video display coupled to the processor circuitry and configured to display the video image of the illuminated target site, the processor circuitry being further configured to suppress the video image in response to the first determination, such that the video display does not display the video image when the flashing event is occurring.

11. The laser tissue ablation system of claim 10, wherein the processor circuitry is further configured to:

form a second determination, from spectral measurement of the return light that indicates that the flashing event light is no longer present in the return light, that the flashing event has ceased; and resume displaying the video image on the video display, in response to forming the second determination.

12. A method for operating a laser tissue ablation system, the method comprising:

illuminating, with an illumination light source disposed on a distal end of an endoscope body, a target site with visible light illumination having a visible light illumination spectrum to create an illuminated target site;

capturing, with a video camera disposed on the distal end of the endoscope body, a video image of the illuminated target site;

delivering therapeutic laser light from a distal end of an optical fiber extending distally from the distal end of the endoscope body toward the target site, the therapeutic laser light having at least one therapeutic laser light wavelength;

receiving return light into the distal end of the optical fiber;

performing a spectral measurement of the return light to determine a measured light level in a detection spectral region that does not overlap with the visible light illumination spectrum and does not include the at least one therapeutic laser light wavelength;

comparing, with processor circuitry, the measured light level to a threshold light level;

determining, with the processor circuitry, that the measured light level exceeds the threshold light level; and generating, with the processor circuitry, in response to the determination that the measured light level exceeds the threshold light level, a flashing event data signal that indicates that a flashing event has occurred at the distal end of the optical fiber.

13. The method of claim 12, further comprising:

causing, with the processor circuitry, an actuator to retract the optical fiber proximally with respect to the endoscope body by a specified distance in response to the determination that the measured light level exceeds the threshold light level, the specified distance being sufficient to terminate the flashing event.

14. The method of claim 12, further comprising:

displaying, on a video display coupled to the processor circuitry, the video image of the illuminated target site; and suppressing, with the processor circuitry, the video image in response to the determination that the measured light level exceeds the threshold light level, such that the video display does not display the video image when the flashing event is occurring.

15. The method of claim 12, further comprising:

supplying, with an irrigation regulator coupled to the endoscope, an irrigant to the target site at a controllable irrigation rate; and increasing, with the irrigation regulator, the irrigation rate in response to the determination that the measured light level exceeds the threshold light level.

16. A laser tissue ablation system, comprising:

an endoscope having an endoscope body;

an illumination light source disposed on a distal end of the endoscope body and configured to illuminate a target site with visible light illumination having a visible light illumination spectral range to create an illuminated target site;

a video camera disposed on the distal end of the endoscope body and configured to capture a video image of the illuminated target site;

a video display configured to display the video image of the illuminated target site;

an optical fiber extending from the endoscope body and configured to:

deliver therapeutic laser light from a distal end of the optical fiber toward the target site, the therapeutic laser light having at least one therapeutic laser light wavelength; and receive return light into the distal end of the optical fiber;

a spectrometer configured to spectrally measure the return light;

processor circuitry configured to:

determine, from the spectral measurement of the return light, when a light level of the return light at at least one flashing event wavelength has increased over a threshold light level, the at least one flashing event wavelength being different from the at least one therapeutic laser light wavelength and being outside the visible light illumination spectral range; and generate, in response to a determination that the light level has increased over the threshold light level, a flashing event data signal that indicates that a flashing event has occurred at the distal end of the optical fiber; and an actuator controllable by the processor circuitry, the actuator configured to automatically retract the optical fiber proximally with respect to the endoscope body by a specified distance in response to the determination that the light level has increased over the threshold light level, the specified distance being sufficient to terminate the flashing event.

17. The laser tissue ablation system of claim 16, further comprising an irrigation regulator coupled to the endoscope and configured to supply an irrigant to the target site at a controllable irrigation rate, the processor circuitry being further configured to increase the irrigation rate in response to the determination that the light level has increased over the threshold light level.

18. A laser tissue ablation system, comprising:

an endoscope having an endoscope body;

an illumination light source disposed on a distal end of the endoscope body and configured to illuminate a target site with visible light illumination having a visible light illumination spectral range to create an illuminated target site;

a video camera disposed on the distal end of the endoscope body and configured to capture a video image of the illuminated target site;

a video display configured to display the video image of the illuminated target site;

an optical fiber extending from the endoscope body and configured to:

deliver therapeutic laser light from a distal end of the optical fiber toward the target site, the therapeutic laser light having at least one therapeutic laser light wavelength; and receive return light into the distal end of the optical fiber;

a spectrometer configured to spectrally measure the return light; and processor circuitry configured to:

determine, from the spectral measurement of the return light, when a light level of the return light at at least one flashing event wavelength has increased over a threshold light level, the at least one flashing event wavelength being different from the at least one therapeutic laser light wavelength and being outside the visible light illumination spectral range; and generate, in response to a determination that the light level has increased over the threshold light level, a flashing event data signal that indicates that a flashing event has occurred at the distal end of the optical fiber, wherein the processor circuitry is further configured to suppress the video image in response to the determination that the light level has increased over the threshold light level, such that the video display does not display the video image when the flashing event is occurring.

* * * * *